United States Patent [19]

Brouwer et al.

[11] Patent Number: 4,783,485
[45] Date of Patent: * Nov. 8, 1988

[54] BENZOYLUREA COMPOUNDS, AND INSECTICIDAL AND ACARICIDAL COMPOSITIONS COMPRISING SAME

[75] Inventors: Marius S. Brouwer; Arnoldus C. Grosscurt; Roelof Van Hes, all of Weesp, Netherlands

[73] Assignee: Duphar International Research B.V., Weesp, Netherlands

[*] Notice: The portion of the term of this patent subsequent to Apr. 7, 2004 has been disclaimed.

[21] Appl. No.: 912,169

[22] Filed: Sep. 26, 1986

Related U.S. Application Data

[63] Continuation of Ser. No. 753,042, Jul. 2, 1985, abandoned, which is a continuation-in-part of Ser. No. 572,142, Jan. 19, 1984, abandoned.

[30] Foreign Application Priority Data

Jan. 24, 1983 [NL] Netherlands .................. 8300239
Jul. 5, 1984 [NL] Netherlands .................. 8402137

[51] Int. Cl.$^4$ ............... A01N 47/36; A01N 47/34; C07C 127/22
[52] U.S. Cl. .................. 514/535; 514/353; 514/539; 514/594; 514/349; 546/297; 546/306; 564/44; 560/27; 560/34
[58] Field of Search .............. 514/594, 539, 535; 564/44; 560/34

[56] References Cited

U.S. PATENT DOCUMENTS

| | | | |
|---|---|---|---|
| 4,013,717 | 3/1977 | Wellinga et al. | 564/44 |
| 4,234,600 | 11/1980 | Sirrenberg et al. | 514/535 |
| 4,275,077 | 6/1981 | Becher et al. | 564/44 |
| 4,276,309 | 6/1981 | Franke et al. | 564/44 X |
| 4,350,706 | 9/1982 | Brouwer et al. | 564/44 |
| 4,426,385 | 1/1984 | Cain | 564/44 |
| 4,472,434 | 9/1984 | Franke et al. | 564/44 X |
| 4,533,676 | 8/1985 | Sirrenberg et al. | 514/535 |
| 4,599,356 | 7/1986 | Lange et al. | 514/535 |
| 4,656,193 | 4/1987 | Lange et al. | 564/44 X |
| 4,699,923 | 10/1987 | Lange et al. | 514/535 |

FOREIGN PATENT DOCUMENTS

| | | |
|---|---|---|
| 13414 | 7/1980 | European Pat. Off. . |
| 56124 | 7/1982 | European Pat. Off. . |
| 69288 | 1/1983 | European Pat. Off. . |
| 167197 | 1/1986 | European Pat. Off. ............. 564/44 |
| 3133009 | 4/1982 | Fed. Rep. of Germany . |
| 3334224 | 4/1985 | Fed. Rep. of Germany . |

7105350 10/1972 Netherlands .

Primary Examiner—Glennon H. Hollrah
Assistant Examiner—Carolyn S. Greason
Attorney, Agent, or Firm—Stevens, Davis, Miller & Mosher

[57] ABSTRACT

The invention relates to new benzoylurea compounds having insecticidal and acaricidal activity, of the general formula

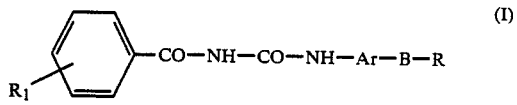

(I)

wherein $R_1$ is a hydrogen atom or represents 1 or 2 halogen atoms;

Ar is a para-phenylene group or a para-pyridylene group, which groups may be substituted with 1 or 2 substituents selected from the group consisting of chlorine, methyl and trifluoromethyl;

B is an oxygen atom or represents a group having the formula

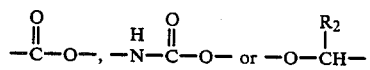

wherein $R_2$ is a hydrogen atom or an alkyl group having 1-4 carbon atoms; and R is a cycloalkyl group or a cycloalkenyl group having 6-12 carbon atoms, which groups may be substituted with 1-3 substituents selected from the group consisting of alkyl and alkenyl having 1-6 carbon atoms, or wherein R is a bi- or polycyclic, saturated or unsaturated, hydrocarbyl group, having 8-14 carbon atoms and, if desired, substituted with 1-3 substituents selected from the group consisting of alkyl and alkenyl having 1-6 carbon atoms;

with the proviso, that, if Ar is a whether or not substituted para-phenylene group, and R is a whether or not substituted cyclohexyl-group, or a saturated bi- or polycyclic hydrocarbyl group having 8-14 carbon atoms, then B does not represent an oxygen atom.

2 Claims, No Drawings

BENZOYLUREA COMPOUNDS, AND INSECTICIDAL AND ACARICIDAL COMPOSITIONS COMPRISING SAME

REFERENCE TO RELATED APPLICATIONS

This application is a continuation of application Ser. No. 753,042, filed 7/2/85, now abandoned, which in turn is a continuation-in-part of application Ser. No. 572,142, filed 1/19/84 and now abandoned.

BACKGROUND OF THE INVENTION

The invention relates to new benzoylurea compounds and to a method of preparing said compounds. The invention also relates to compositions having insecticidal and acaricidal activity and comprising these compounds, and to the use of said compositions for controlling insects and/or mites.

It is already known that certain N-benzoyl-N'-phenylurea compounds have an insecticidal activity. From Netherlands patent application No. 7105350 in the name of Applicants it appears that in particular the substitution pattern of the benzoyl group has an important influence on said activity. In general, a high insecticidal activity is found in benzoylurea compounds the benzoyl group of which is substituted in the 2- or 2,6-positions, for example, with one or two halogen atoms. Substituents on the other side of the molecule, so in the N'-phenyl ring, are less essential for the insecticidal activity but can nevertheless influence said activity in such manner that the benzoylurea compound is better or worse suitable for practical applications. For example, it appears from an article by Wellinga et al. in J. Arg. Food Chem., Vol. 21, No. 3, 1973, pp. 348–354 that electrons-donating substituents at the N'-phenyl ring, for example, a methoxy group, adversely influence the insecticidal activity.

It has surprisingly been found, that N'-phenyl benzoylurea compounds, to the phenyl group of which are attached via an oxygen bridge, an oxycarbonyl bridge, an oxycarbonylamino bridge or an alkoxy bridge a whether or not substituted cycloalkyl or cycloalkenyl group or a bi- or polycyclic hydrocarbyl group, have an interesting insecticidal activity. Moreover, an acaricidal activity is also found in the new benzoylurea compounds according to the invention.

Chemically related benzoylurea compounds are described in the Netherlands patent application No. 7905155 in the name of Applicants, e.g. N-(2-chlorobenzoyl)-N'-[4-(1-phenylcyclohexyloxy)phenyl]urea.

As will be clear from the Examples, this known compound is considerably less active than the new compounds of the present invention.

The invention relates to benzoylurea compounds of the general formula

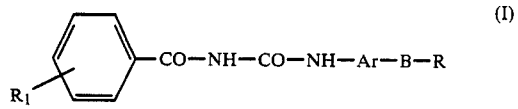

wherein
$R_1$ is a hydrogen atom or represents 1 or 2 halogen atoms;
Ar is a para-phenylene group or a para-pyridylene group, which groups may be substituted with 1 or 2 substituents selected from the group consisting of chlorine, methyl and trifluoromethyl;
B is an oxygen atom or represents a group having the formula

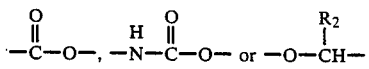

wherein $R_2$ is a hydrogen atom or an alkyl group having 1–4 carbon atoms; and
R is a cycloalkyl group or a cycloalkenyl group having 6–12 carbon atoms, which groups may be substituted with 1–3 substituents selected from the group consisting of alkyl and alkenyl having 1–6 carbon atoms, or wherein
R is a bi- or polycyclic, saturated or unsaturated, hydrocarbyl group, having 8–14 carbon atoms and, if desired, substituted with 1–3 substituents selected from the group consisting of alkyl and alkenyl having 1–6 carbon atoms;
with the proviso, that,
if Ar is a whether or not substituted para-phenylene group, and
R is a whether or not substituted cyclohexyl group, or a saturated bi- or polycyclic hydrocarbyl group having 8–14 carbon atoms, then B does not represent an oxygen atom.

These compounds have an interesting insecticidal and acaricidal activity as will become apparent from the examples.

Benzoylurea compounds of the general formulae

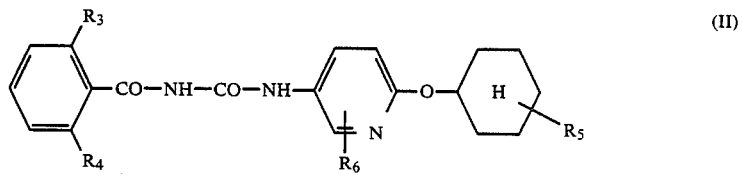

or

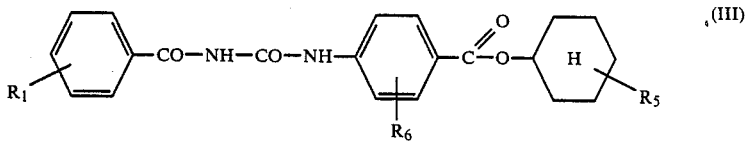

wherein
$R_1$ has the above meaning,
$R_3$ is a hydrogen atom or a halogen atom, $R_4$ is a halogen atom, $R_5$ represents 1-3 alkyl or alkenyl groups having 1-6 carbon atoms, and $R_6$ is a hydrogen atom or represents 1 or 2 substituents selected from the group consisting of chlorine, methyl and trifluoromethyl, are to be preferred on account of their high insecticidal activities.

Various compounds of the invention may occur in two stereoisomers, namely the d- and the l-form, while of course mixtures of these stereoisomers are also possible. If desired, the stereoisomers can be separated from each other by methods known for this purpose, but for practical considerations the use of a sterically pure starting material is to be preferred for the preparation of one of the stereoisomers in a pure form.

Examples of new benzoylurea compounds according to the invention are:

(1) N-(2-chlorobenzoyl)-N'-(2-l-menthyloxy-5-pyridyl)urea,
(2) N-(2,6-difluorobenzoyl)-N'-(2-l-menthyloxy-5-pyridyl)urea,
(3) N-benzoyl-N'-(4-dl-menthyloxycarbonylphenyl)urea,
(4) N-(2-chlorobenzoyl)-N'-(4-dl-menthyloxycarbonylphenyl)urea,
(5) N-(2,6-difluorobenzoyl)-N'-(4-dl-menthyloxycarbonylphenyl)urea
(6) N-(2-chlorbenzoyl)-N'-(4-dl-menthyloxycarbonylaminophenyl)urea,
(7) N-(2,6-difluorobenzoyl)-N'-(4-dl-menthyloxycarbonylaminophenyl)urea,
(8) N-(2,6-difluorobenzoyl)-N'-(4-cyclododecyloxyphenyl)urea,
(9) N-(2,6-difluorobenzoyl)-N'-(4-myrtenyloxyphenyl)urea,
(10) N-(2,6-difluorobenzoyl)-N'-[4-(2-isopropylcyclohexyloxycarbonyl)phenyl]urea,
(11) N-(2-chlorobenzoyl)-N'-[4-(2-isopropylcyclohexyloxycarbonyl)phenyl]urea,
(12) N-(2-chlorobenzoyl)-N'-[4-(3,5,5-trimethylcyclohexen-2-yloxy)phenyl]urea,
(13) N-(2,6-difluorobenzoyl)-N'-[4-(3,5,5-trimethylcyclohexen-2-yloxy)phenyl]urea,
(14) N-(2-chlorobenzoyl)-N'-[4-(1-cyclohexyl-n-butoxy)phenyl]urea,
(15) N-(2,6-difluorobenzoyl)-N'-[4-(1-cyclohexyl-n-butoxy)phenyl]urea,
(16) N-(2-chlorobenzoyl)-N'-[4-(1-cyclohexyl-2-methyl-n-propoxy)phenyl]urea,
(17) N-(2,6-difluorobenzoyl)-N'-[4-(1-cyclohexyl-2-methyl-n-propoxy)phenyl]urea,
(18) N-(2-chlorobenzoyl)-N'-[3,5-dichloro-4-(1-cyclohexyl-n-butoxy)phenyl]urea, and
(19) N-(2,6-difluorobenzoyl)-N'-[3,5-dichloro-4-(1-cyclohexyl-n-butoxy)phenyl]urea.

Related benzoylurea compounds are the subject of the non-prepublished European patent application No. 832018634 in the name of the Applicant.

The substances according to the invention may be used for the control of insects in agriculture and horticulture, in forests and in surface water, as well as for the protection of textile against attack by, for example, moths and carpet beetles, against insects in stocks, for example, in stored cereals, and against insects in the veterinary and medical-hygienic sectors.

The substances according to the invention may also be used for the control of insects living in the manure of warm-blooded animals, such as cows, pigs and hens. For this application the active compounds can be administered orally to the animals, for example, mixed through the food, so that they land in the manure after some time ("through-feeding").

The compounds according to the invention are particularly active against larvae and eggs of insects. In principle, the compounds may be used against all insects mentioned in Pestic. Sci. 9, 373–386 (1978).

For practical pesticidal application the substances in accordance with the invention are usually processed in compositions. In such compositions the active substance is mixed with solid carrier material or dissolved or dispersed in liquid carrier material, if desired in combination with auxiliary substances, for example, emulsufiers, wetting agents, dispersible agents and stabilizers.

Examples of compositions according to the invention are aqueous solutions and dispersions, oily solutions and oily dispersions, solutions in organic solvents, pastes, dusting powders, dispersible powders, miscible oils, granules, pellets and aerosol compositions.

Dispersible powders, pastes and miscible oils are compositions in concentrate form which are diluted prior to or during use.

The invert emulsions and solutions in organic solvents are mainly used in air application, namely when large areas are treated with a comparatively small quantity of composition. The invert emulsion can be prepared shortly before or even during spraying in the spraying apparatus be emulsifying water in an oily solution or an oily dispersion of the active substance. The solutions of the active substance in organic solvents may be provided with a phytotoxicity-reducing substance, for example, wool fat, wool fatty acid or wool fatty alcohol.

A few forms of compositions will be described in more detail hereinafter by way of example.

Granular compositions are prepared by taking up, for example, the active substance in a solvent or dispersing it in a diluent and impregnating the resulting solution/suspension, if desired in the presence of a binder, on granular carrier material, for example porous granules (for example pumice and attaclay), mineral non-porous granules (sand or ground marl), organic granules (for example, dried coffee grounds, cut tobacco stems or ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then with liquid to the desired particle size.

Dusting powders can be obtained by intimately mixing the active substance with an inert solid powdered carrier material, for example, talcum.

Dispersable powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight or a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution. Suitable solvents are, for example, xylene, toluene, petroleum distillates which are rich in aromates, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight.

In addition to a miscible oil may also be mentioned as a liquid and highly concentrated primary composition a solution of the active substance in a readily water-miscible liquid, for example, a glycol, a glycol ether, dimethylformamide, or N-methylpyrrolidone, to which solution a dispersing agent, and if desired, a surface-active substance has been added. When diluting with water shortly before or during spraying, an aqueous dispersion of the active substance is then obtained.

An aerosol composition according to the invention is obtained in the usual manner by incorporation the active substance, if desired in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

Fumigating candles or fumigating powders, i.e. compositions which, while burning, can generate a pesticidal smoke, are obtained by taking up the active substance in a combustible mixture which may contain as a fuel a sugar or a wood, preferably in a ground form, a substance to maintain combustion, for example, ammonium nitrate or potassium chlorate, and furthermore a substance to delay combustion, for example, kaolin, bentonite and/or colloidal silicic acid.

In addition to the above-mentioned ingredients, the agents according to the invention may also contain other substances known for use in this type of agents. For example a lubricant, e.g., calcium stearate or magnesium stearate, may be added to a dispersible powder or a mixture to be granulated. "Adhesives", for example, polyvinylalcohol, cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Pesticidal compounds known per se may also be incorporated in the compositions according to the invention. As a result of this the activity spectrum of the composition is widened and synergism may occur.

For use in such a combination composition are to be considered the following known insecticidal, acaricidal and fungicidal compounds:

Insectides, for example:
1. organic chlorine compounds, for example 6,7,8,9,10,10-hexachloro-1,5,5a,6,9a-hexahydro-6,9-methano-2,4,3-benzo[e]-dioxathiepine-3-oxide;
2. carbamates, for example, 2-dimethylamino-5,6-dimethylpyrimidin-4-yl dimethyl carbamate and 2-isopropoxyphenyl methylcarbamate;
3. di(m)ethylphosphates, for example, 2-chloro-2-diethylcarbamoyl-1-methylvinyl-, 2-methoxycarbonyl-1-methylvinyl-, 2-chloro-1-(2,4-dichlorophenyl)vinyl-, and 2-chloro-1-(2,4,5-trichlorophenyl)vinyl di(m)ethylphosphate;
4. O,O-di(m)ethyl phosphorothioates, for example, O(S)-2-methylthioethyl-, S-2-ethylsulphinylethyl-, S-2-(1-methylcarbamoylethylthio)ethyl-, O-4-bromo-2,5-dichlorophenyl-, O-3,5,6-trichloro-2-pyridyl-, O-2-isopropyl-6-methylpyrimidin-4-yl-, and O-4-nitrophenyl O,O-di(m)ethyl phosphorothioate;
5. O,O-di(m)ethyl phosphorodithioates, for example, S-methylcarbamoylmethyl-, S-2-ethylthioethyl-, S-(3,4-dihydro-4-oxobenzo[d]-1,2,3-triazin-3-ylmethyl)-, S-1,2-di(ethoxycarbonyl)ethyl-, S-6-chloro-2-oxobenzoxazolin-3-ylmethyl-, and S-2,3-dihydro-5-methoxy-2-oxo-1,3,4-thiadiazol-3-ylmethyl O,O-di(m)ethylphosphorodithioate;
6. phosphonates, for example, dimethyl 2,2,2-trichloro-1-hydroxyethylphosphonate;
7. natural and synthetic pyrethroids;
8. amidines, for example, N'-(2-methyl-4-chlorophenyl)-N,N-dimethylformamidine;
9. microbial insecticides, such as Bacillus thuringiensis;
10. carbamoyl-oximes, such as S-methyl N-(methylcarbamoyloxy)thioacetamidate; and
11. other benzoylurea compounds, such as N-(2,6-difluorobenzoyl)-N'-(4-chlorophenyl)urea.

Acaricides, for example:
1. organic tin compounds, for example, tricyclohexyl tin hydroxide and di[tri-(2-methyl-2-phenylpropyl)tin]oxide;
2. organic halogen compounds, for example isopropyl 4,4'-dibromobenzilate, 2,2,2-trichloro-1,1-di(4-chlorphenyl)ethanol and 2,4,5,4'-tetrachlorodiphenyl sulphone;
3. synthetic pyrethroids,
and furthermore: 3-chloro-α-ethoxyimino-2,6-dimethoxybenzyl benzoate and O,O-dimethyl S-methylcarbamoyl methyl phosphorothioate.

Fungicides, for example:
1. organic tin compounds, for example, triphenyl tin hydroxide and triphenyl tin acetate;
2. alkylene bisdithiocarbamates, for example, zinc ethylenebisdithiocarbamate and manganese ethylene bisdithiocarbamate;
3. 1-acyl- or 1-carbamoyl-N-benzimidazole (-2) carbamates and 1,2-bis(3-alkoxycarbonyl-2-thiureido)benzene;
and furthermore 2,4-dinitro-6-(2-octylphenylcrotonate); 1-[bis(dimethylamino)phosphoryl]-3-phenyl-5-amino-1,2,4-triazole; N-trichloromethylthiophthalimide; N-trichloromethylthiotetrahydrophthalimide; N-(1,1,2,2-tetrachloroethylthio)-tetrahydrophthalimide; N-dichlorofluoromethylthio-N-phenyl-N,N'-dimethylsulphamide; tetrachloroisophthalonitrile; 2-(4'-thiazolyl)benzimidazole; 5-butyl-2-ethylamino-6-methylpyrimidine-4-yl-dimethylsulphamate; 1-(4-chlorophenoxy)-3,3-dimethyl-1(1,2,4-triazole-1-yl)-2-butanone; α-(2-chlorophenyl)-α-(4-chlorophenyl)-5-pyrimidinemethanol; 1-(isopropylcarbamoyl)-3-(3,5-dichlorophenyl)hydantoin; N-(1,1,2,2-tetrachloroethylthio)-4-cyclohexene-1,2-carboximide; N-trichloromethylmercapto-4-cyclohexene-1,2-dicarboximide; N-tridecyl-2,6-dimethylmorpholine; metal salts of ethylphosphite; and N-(2,6-dimethylphenyl-N-methoxyacetyl)alanine methylester; or mixtures of these compounds.

The dosage of the insecticidal composition according to the invention desired for practical application will, of course, depend on various factors, for example, application area, selected active material, composition form, nature and extent of the infection, and the weather conditions.

In general it holds that favourable results are achieved with a dosage which corresponds to 1 to 5,000 g of the active substance per hectare.

For the above-described "through-feeding" the active substance is mixed through the food in a quantity which is effective for insecticidal applications.

The compounds according to the invention are novel substances which can be prepared in a manner known per se for related compounds.

For example, the compounds according to the invention can be prepared by reacting a substituted aniline of the general formula

R—B—Ar—NH$_2$ wherein R, B and Ar have the above meanings, with a benzoylisocyanate of the general formula

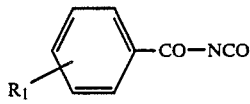

wherein R$_1$ also has the above meaning.

The novel compounds according to the invention can also be prepared by reacting a substituted benzamide of the general formula

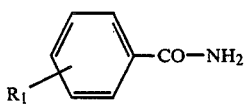

wherein R$_1$ has the above meaning, with an isocyanate of the general formula

R—B—Ar—NCO wherein R$_1$, B and Ar also have the above meanings.

The above reactions are preferably carried out in the presence of an organic solvent, for example, an aromatic hydrocarbon, an alkyl halide, a cyclic or non-cyclic dialkyl ether, or acetonitrile, at a reaction temperature between 0° C. and the boiling-point of the solvent used.

Although the above-indicated methods of preparation are the best suitable, the novel compounds may also be prepared in a different way, for example, as described in the above-mentioned Netherlands patent application No. 7105350 or according to the methods described in Netherlands patent application No. 7806678 or No. 8005588.

The invention will now be described in greater detail with reference to the ensuing specific examples.

EXAMPLE I

Preparation of
N-(2,6-difluorobenzoyl)-N'-(4-dl-menthyloxycarbonylphenyl)urea. (5)

0.92 g of 2,6-difluorobenzoylisocyanate were added to a solution of 1.37 g of 4-dl-menthyloxycarbonylaniline in 50 ml of dry diethyl ether while stirring at room temperature.

After stirring for an additional half hour and adding 50 ml of petroleum ether (40-60) the formed precipitate was sucked off, washed with petroleum ether and dried. The desired product was obtained in a yield of 2.0 g; melting-point 169°–170° C. The starting aniline was obtained from the corresponding nitro compound by reduction with hydrogen under the influence of Raney nickel as a catalyst, ethyl acetate being used as a solvent. 1-Nitro-4-dl-methyloxycarbonylbenzene was prepared by reaction of dl-menthol with 4-nitrobenzoylchloride.

In a corresponding manner, in which if desired, instead of diethyl ether acetonitrile was used as a solvent for the urea-formation, the following compounds were prepared; the compound numbers correspond with the numbers given before in the specification:

| compound no. | melting point |
|---|---|
| 1 | 174–176° C. |
| 2 | 144–147° C. |
| 3 | 222–223° C. |
| 4 | 195–196° C. |
| 5 | 169–170° C. |
| 6 | 193–196° C. |
| 7 | 196–202° C. |
| 8 | 172–184° C. |
| 9 | 168–169° C. |
| 10 | 203–205° C. |
| 11 | 162–163° C. |
| 12 | 189–190° C. |
| 13 | 182–183° C. |
| 14 | 54–57° C. |
| 15 | 123–130° C. |
| 16 | 133–141° C. |
| 17 | 116–123° C. |
| 18 | 154–166° C. |
| 19 | 98–110° C. |

EXAMPLE II (a) Preparation of a solution of an active substance, namely

N-(2,6-difluorobenzoyl)-N'-(4-l-menthyloxy-5-pyridyl)urea (2), in a water-miscible liquid ("liquid").

10 g of the above active substance were dissolved in a mixture of 10 ml of isophorone and approximately 70 ml of dimethylformamide, after which polyoxyethylene glycol ricinyl ether as an emulsifier was added in a quantity of 10 g.

The other active substances were processed to 10% or 20% "liquids" in a corresponding manner. In a corresponding manner, "liquids" were obtained in N-methylpyrrolidone, dimethylformamide, and a mixture of N-methylpyrrolidone and isophorone as solvents.

(b) Preparation of a solution of the active substance in an organic solvent 200 mg of the active substance to be investigated were dissolved in 1,000 ml of acetone in the presence of 1.6 g of nonylphenolpolyoxyethylene. After pouring in water, this solution may be used as a spraying liquid.

(c) Preparation of an emulsifiable concentrate of the active substance 10 g of the active substance to be investigated were dissolved in a mixture of 15 ml of isophorone and 70 ml of xylene; 5 g of a mixture of a polyoxyethylene sorbitan ester and an alkyl benzene sulphonate as an emulsifier were added to this solution.

(d) Preparation of a dispersible powder (W.P.) of the active substance 25 g of the active substance to be investigated were mixed with 68 g of kaolin in the presence of 2 g of sodium butylnaphthalene sulphonate and 5 g of lignine sulphonate.

(e) Preparation of a suspension concentrate (flowable) of the active substance

A mixture of 10 g of active substance, 2 g of lignine sulphonate and 0.8 g of sodium alkylsulphate were supplied with water till a total amount of 100 ml.

(f) Preparation of a granule of the active substance 7.5 g of active substance, 5 g of sulphite lye and 87.5 g of ground dolomite were mixed, after which the resulting mixture was processed to a granular composition by means of the so-called compacting method.

EXAMPLE III

Young Brussels sprouts plants, approximately 15 cm high, were sprayed till run-off with compositions obtained according to Example II (b) in various concentrations; to these compositions had been added in addition approximately 250 mg of an alkylated phenol polyoxyethylene compound (Citowett) per liter. After the plants had dried, they were placed in cylinders of plexiglass and then infected with 5 larvae of *Pieris brassicae* (cabbage white butterfly) in the third larval stage (L3). The cylinders were then covered with a gauze and stored, an alternating light-dark cycle of 16 hours light and 8 hours dark being used; temperature in the light 24° C., rel. humidity (RH) 70%; temperature in the dark 19° C. 80–90% RH. After 5 days the mortality percentage of the larvae was established. Each experiment was carried out in triplicate. The average results of the experiments are recorded in Table A below. The meanings of the symbols in the table are as follows:
+ =90–100% mortality
± =50–90% mortality
− =<50% mortality
N-(2-chlorobenzoyl)-N'-4-(1-phenylcyclohexyloxy)-phenyl urea ("known") has been included in the tests by way of comparison.

TABLE A

| Insecticidal activity against larvae (L3) of *Pieris brassicae* | | | | | | | | | |
|---|---|---|---|---|---|---|---|---|---|
| | Concentration in mg of active substance per liter | | | | | | | | |
| Comp. no. | 300 | 100 | 30 | 10 | 3 | 1 | 0.3 | 0.1 | 0.03 |
| (1) | + | + | + | + | + | + | − | | |
| (2) | + | + | + | + | + | + | + | ± | − |
| (3) | + | + | + | + | + | | | | |
| (4) | + | + | + | + | + | | | | |
| (5) | + | + | + | + | + | + | + | | |
| (6) | + | + | + | + | + | − | | | |
| (7) | + | + | + | + | + | ± | − | | |
| (8) | + | + | + | + | + | + | + | | |
| (10) | + | + | + | + | + | + | + | | |
| (12) | + | + | + | + | + | + | + | | |
| (13) | + | + | + | + | + | + | + | | |
| "known" | + | + | − | | | | | | |

Note: If the test results do not finish with a "−" sign, the tests have not been completed.

Liquid insecticidal compositions are used in practice in quantities of approximately 1,000 liters per hectare. The coverage of the plants with the composition, however, is considerably less good in practice than in a laboratory or glasshouse experiment as described herein before. It has hence been found that in practice the dose is to be increased by a factor 10 to obtain the same efficiency.

So in practical applications the above quantities with insecticidal activity correspond to approximately 3 to approximately 3,000 g of active substance per hectare.

EXAMPLE IV

20 Larvae of *Aedes aegypti* (yellow-fever mosquito) were placed in various concentrations of aqueous suspensions of the active substances obtained according to example II (e). The suspensions were kept at a temperature of 25° C. for 10 days, during which incubation period the larvae were fed with an aqueous suspension of powdered brown bread and yeast. After 10 days the mortality percentage was determined taking the natural mortality into account. The results of the experiment are recorded in Table B. The meaning of the symbols is the same as in Example III.

TABLE B

| Insecticidal activity against larvae (L1) of *Aedes aegypti* | | | | | | | |
|---|---|---|---|---|---|---|---|
| | Concentration in mg of active substance per liter | | | | | | |
| Comp. no. | 1 | 0.3 | 0.1 | 0.03 | 0.01 | 0.003 | 0.001 |
| (2) | + | + | + | + | + | + | − |
| (7) | + | + | + | − | | | |
| (8) | + | + | + | + | + | ± | − |
| (12) | + | + | + | ± | ± | − | |
| (13) | + | + | + | + | + | ± | − |
| (15) | + | + | + | + | − | | |
| (17) | + | + | + | + | − | | |
| (18) | + | + | + | + | − | | |
| (19) | + | + | + | + | − | | |

EXAMPLE V

The growth tops of broad beans were removed in such a way that four well developed leaves remained. The plants were sprayed till run-off with compositions obtained according to Example II (b) in various concentrations; to these compositions had moreover been added approximately 250 mg of Citowett per liter. After the plants had dried, they were placed in perspex cylinders and then infected with 5 larvae of *Spodoptera littoralis* (Egyptian cotton leafworm) in the third larval stage (L3). The cylinders were then covered with a gauze and then stored as described in Example III. After 5 days the mortality percentage of the larvae was established. Each experiment was carried out in triplicate. The average results of the experiments are recorded in table C. The meanings of the symbols are the same as in Example III.

TABLE C

| Insecticidal activity against larvae (L3) of *Spodoptera littoralis* | | | | | | | |
|---|---|---|---|---|---|---|---|
| | Concentration in mg of active substance per liter | | | | | | |
| Comp. no. | 300 | 100 | 30 | 10 | 3 | 1 | 0.3 |
| (1) | + | + | + | + | + | ± | − |
| (2) | + | + | + | + | + | ± | − |
| (3) | + | + | + | + | + | − | |
| (4) | + | + | + | + | + | + | − |
| (5) | + | + | + | + | + | ± | |
| (6) | + | + | + | ± | ± | − | |
| (7) | + | + | + | + | − | | |
| (8) | + | + | + | ± | ± | | |
| (9) | + | + | ± | | | | |
| (10) | + | + | + | + | + | + | ± |
| (13) | + | + | + | + | ± | ± | − |

In practice the above quantities with insecticidal activity correspond to approx. 10 to approx. 3,000 g of active substance per liter.

EXAMPLE VI

Young potato plants, approx. 15 cm high, were sprayed with the compositions obtained according to Example II (b) in various concentrations; in addition approx. 250 mg of Citowett per liter had been added to these compositions. After the plants had dried, plexiglass cylinders were placed over the plants. The plants were then infected with 10 larvae of *Leptinotarsa decemlineata* (Colorado potato beetle) in the third larval stage (L3). The infected plants were stored as indicated in Example III. After 5 days the mortality percentage of the larvae was established. The experiments have been carried out in triplicate. The average results of the experiments are recorded in table D below. The meanings of the symbols are the same as in Example III. The same "known" compound was used as in Example III.

TABLE D

Insecticidal activity against larvae (L3) of *Leptinotarsa decemlineata*

| Comp. no. | Concentration in mg of active substance per liter | | | | | | |
|---|---|---|---|---|---|---|---|
| | 300 | 100 | 30 | 10 | 3 | 1 | 0.3 |
| (2) | + | + | + | + | − | | |
| (3) | + | + | − | | | | |
| (4) | + | + | + | ± | − | | |
| (5) | + | + | + | + | ± | | |
| (6) | + | + | + | − | | | |
| (7) | + | + | + | ± | − | | |
| (8) | + | + | + | + | ± | | |
| (9) | + | + | + | | | | |
| (10) | + | + | + | + | + | | |
| (12) | + | + | + | + | + | + | ± |
| (13) | + | + | + | + | ± | + | ± |
| (14) | + | + | + | − | | | |
| (15) | + | + | + | + | − | | |
| (17) | + | + | + | − | | | |
| (18) | + | + | + | + | ± | | |
| (19) | + | + | + | + | + | | |
| "known" | − | | | | | | |

In practice the above quantities with insecticidal activity correspond with approx. 30 to approx. 3000 grams of active substance per hectare.

EXAMPLE VII

Acaricidal activity against larvae and eggs of *Tetranychus cinnabarinus*

Dwarf French bean plants (Phaseolus vulgaris) having two well developed leaves were infected with *Tetranychus cinnabarinus* (carnation spider mite) by placing a given number of adult female mites on the plants. Two days after the infection the plants with the adult mites present thereon were sprayed till run-off with compositions obtained according to Example II (b) in various concentrations; to these compositions had moreover been added approximately 150 mg of an alkylated phenolpolyoxyethylene compound (Citowett) per liter. 5 Days after spraying, the adult insects were removed from the plants. The plants were stored for 2 weeks in a space with controlled temperature (T) and relative humidity (RH), an alternating light-dark cycle being used of 16 hours light and 8 hours dark. Light: T approximately 24° C., RH approximately 70%; dark: T approximately 19° C., RH 80–90%. The reduction of the population, i.e. the mortality of the larvae and eggs as compared with plants not treated with chemicals was established. The experiment was carried out in triplicate. When using a composition which contained compound (15) as the active substance, a reduction of the population with approx. 100% as compared with plants not treated with chemicals was found.

We claim:

1. A composition having insecticidal and acaricidal activity characterized in that, in addition to a liquid or solid inert carrier material, the composition comprises a compound of the formula IV in an effective amount, said compound of formula IV being a benzoylurea compound of the formula

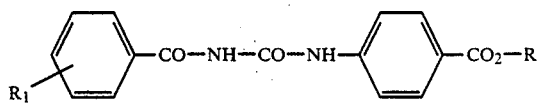

wherein
$R_1$ is a hydrogen atom or represents 1 or 2 halogen atoms; and
R is a cyclohexyl group, a cyclododecyl group, a cyclohexenyl group or a bicycloheptenyl group, any of which groups may be substituted with 1–3 substituents selected from the group consisting of $C_1$–$C_6$ alkyl and $C_2$–$C_6$ alkenyl;
with the proviso, that if R is a cyclohexyl group, then said cyclohexyl group is substituted with 1 or 2 substituents selected from the group consisting of methyl and isopropyl, at least one isopropyl group being positioned in the ortho position.

2. A composition as claimed in claim 1, characterized in that the active constituent is a compound selected from the group consisting of
N-(2-chlorobenzoyl)-N'-(4-menthyloxycarbonylphenyl)urea;
N-2,6-difluorobenzoyl)-N'-(4-menthyloxycarbonylphenyl)urea;
N-(2-chlorobenzoyl)-N'-[4-(2-isopropylcyclohexyloxycarbonyl)phenyl]urea;
N-(2,6-difluorobenzoyl)-N'-[4-(2-isopropylcyclohexyloxycarbonyl)phenyl]urea;
N-(2-chlorobenzoyl)-N'-[4-(3,5,5-trimethylcyclohexenyloxy)phenyl]urea; and
N-(2,6-difluorobenzoyl)-N'-[4-(3,5,5-trimethylcyclohexenyloxy)phenyl]urea.

* * * * *